US011020257B2

(12) United States Patent
Roeder et al.

(10) Patent No.: US 11,020,257 B2
(45) Date of Patent: Jun. 1, 2021

(54) PRE-LOADED MULTIPORT DELIVERY DEVICE

(71) Applicants: Cook Medical Technologies LLC, Bloomington, IN (US); University of Massachusetts Medical School, Worcester, MA (US)

(72) Inventors: Blayne A. Roeder, Bloomington, IN (US); Andres Schanzer, Southborough, MA (US)

(73) Assignees: Cook Medical Technologies LLC, Bloomington, IN (US); University of Massachusetts Medical School, Worcester, MA (US)

( * ) Notice: Subject to any disclaimer, the term of this patent is extended or adjusted under 35 U.S.C. 154(b) by 124 days.

(21) Appl. No.: 16/234,948

(22) Filed: Dec. 28, 2018

(65) Prior Publication Data
US 2019/0201223 A1    Jul. 4, 2019

Related U.S. Application Data

(60) Provisional application No. 62/613,147, filed on Jan. 3, 2018.

(51) Int. Cl.
*A61F 2/954*    (2013.01)
*A61F 2/07*    (2013.01)
(Continued)

(52) U.S. Cl.
CPC ............... *A61F 2/954* (2013.01); *A61F 2/07* (2013.01); *A61F 2/958* (2013.01); *A61F 2/966* (2013.01)

(58) Field of Classification Search
CPC .. A61F 2/954; A61F 2/07; A61F 2/958; A61F 2/966; A61F 2/9517; A61F 2/95;
(Continued)

(56) References Cited

U.S. PATENT DOCUMENTS 7,413,573 B2    8/2008    Hartley et al.
7,435,253 B1    10/2008    Hartley et al.
(Continued)

FOREIGN PATENT DOCUMENTS

| EP | 2745813 A1 | 6/2014 |
| WO | 2009148602 A1 | 12/2009 |
| WO | 2015075708 A1 | 5/2015 |

OTHER PUBLICATIONS

Oxford Concise Medical Dictionary, 2010, Oxford University Press, 8 ed. ; also available at www.oxfordreference.com (Year: 2010).*

*Primary Examiner* — Melanie R Tyson
(74) *Attorney, Agent, or Firm* — Brinks Gilson & Lione

(57) ABSTRACT

A pre-loaded stent graft delivery device and stent graft, the stent graft delivery device. The stent graft has at least one fenestration or side arm and the fenestration is preloaded with an indwelling guide wire. Indwelling access sheaths are provided within auxiliary lumens of a pusher catheter and dilators are preloaded into the access sheaths along with the indwelling guide wire. The auxiliary lumens have an oblong cross-section. A handle assembly at a distal end of the guide wire catheter. The handle includes a multiport manifold with access ports to the auxiliary lumens in the pusher catheter. Upon deployment of the stent graft, the indwelling guide wire can be used to facilitate catheterization of a side branch or target vessel through the fenestration or be used to stabilize the access sheath during catheterization, advancement of the access sheath into the target vessel and deployment of a stent therein.

21 Claims, 15 Drawing Sheets

(51) Int. Cl.
*A61F 2/966* (2013.01)
*A61F 2/958* (2013.01)

(58) Field of Classification Search
CPC .............. A61F 2/962; A61F 2002/9505; A61F 2002/9534; A61F 2002/9665; A61M 25/0032; A61M 25/09; A61M 29/00; A61M 39/06
See application file for complete search history.

(56) References Cited

U.S. PATENT DOCUMENTS

| | | |
|---|---|---|
| 7,914,572 B2 | 3/2011 | Hartley et al. |
| 8,118,854 B2 | 2/2012 | Bowe |
| 8,709,061 B2 * | 4/2014 | Greenberg ................ A61F 2/07 623/1.11 |
| 8,753,385 B2 | 6/2014 | Hartley et al. |
| 8,876,879 B2 | 11/2014 | Hartley et al. |
| 9,504,555 B2 | 11/2016 | Hartley et al. |

* cited by examiner

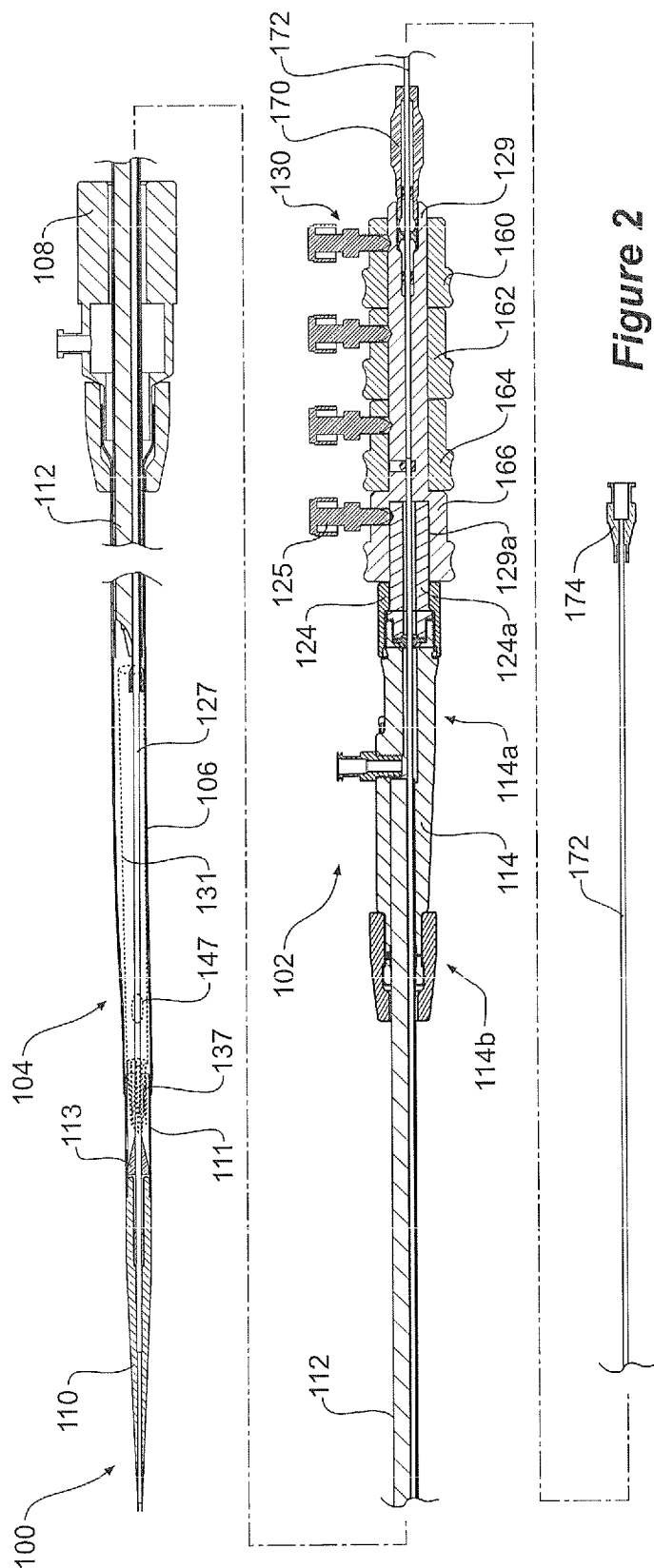
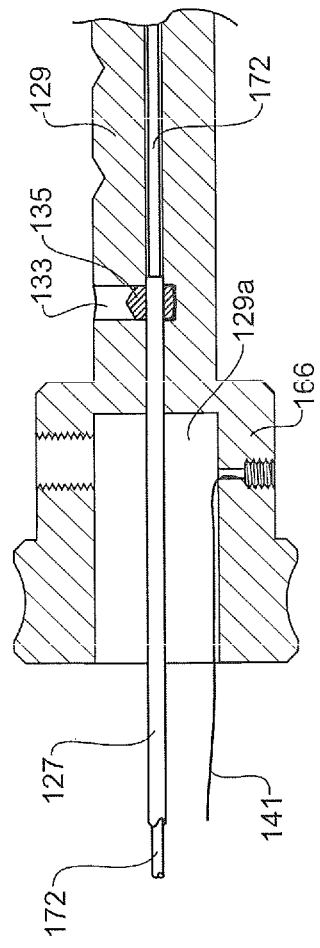
Figure 2
Figure 2A

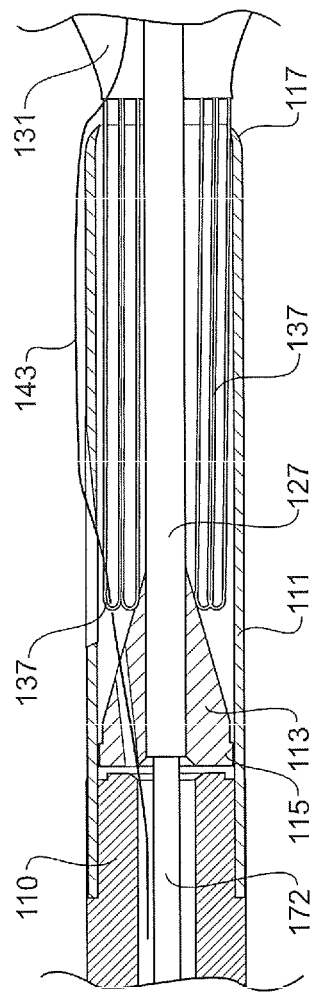
*Figure 2B*
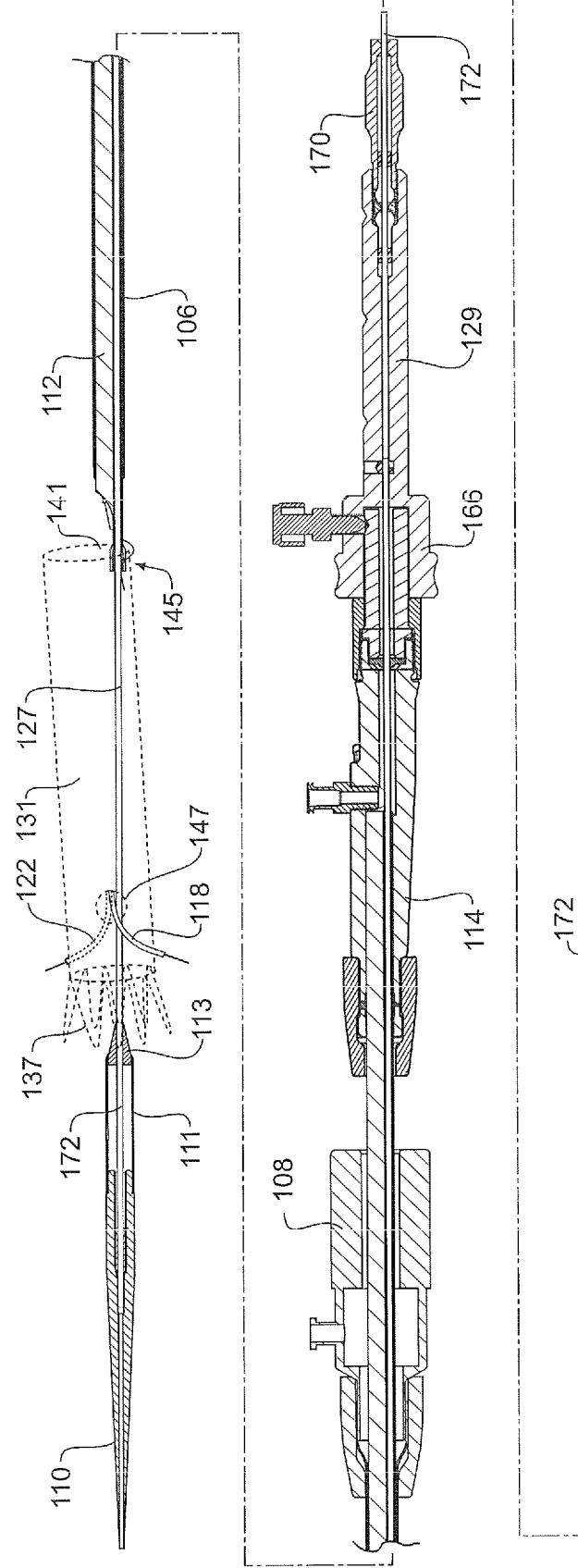
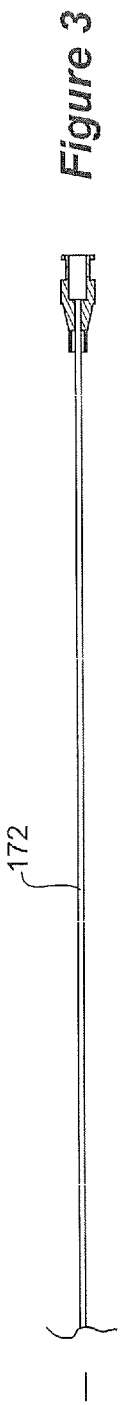
*Figure 3*

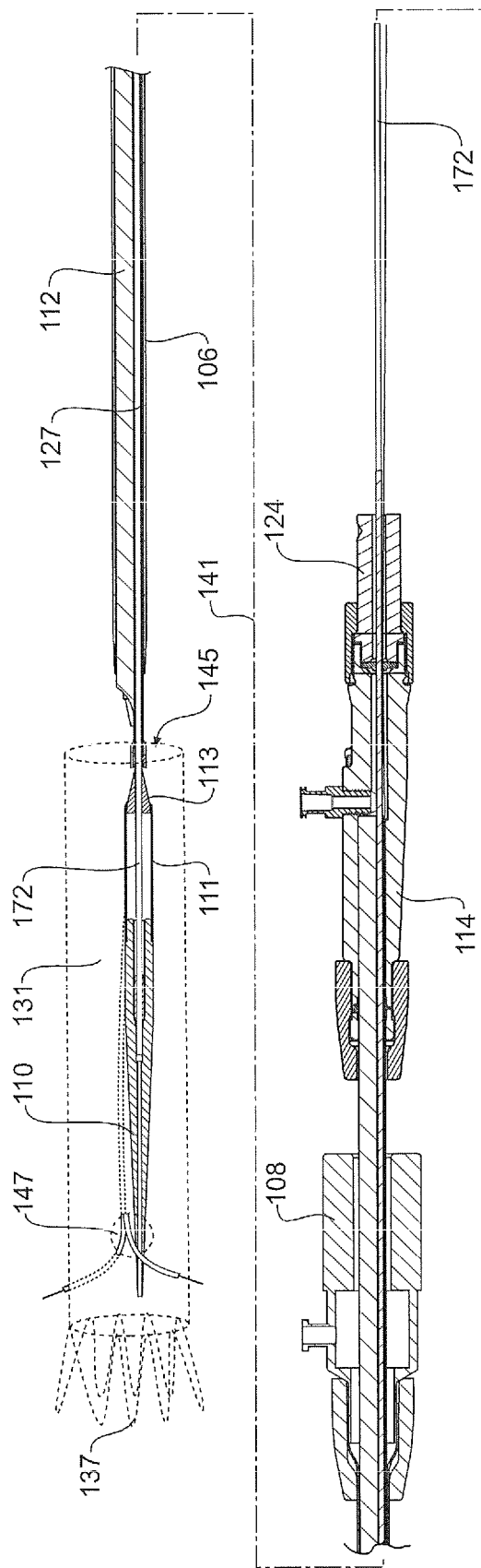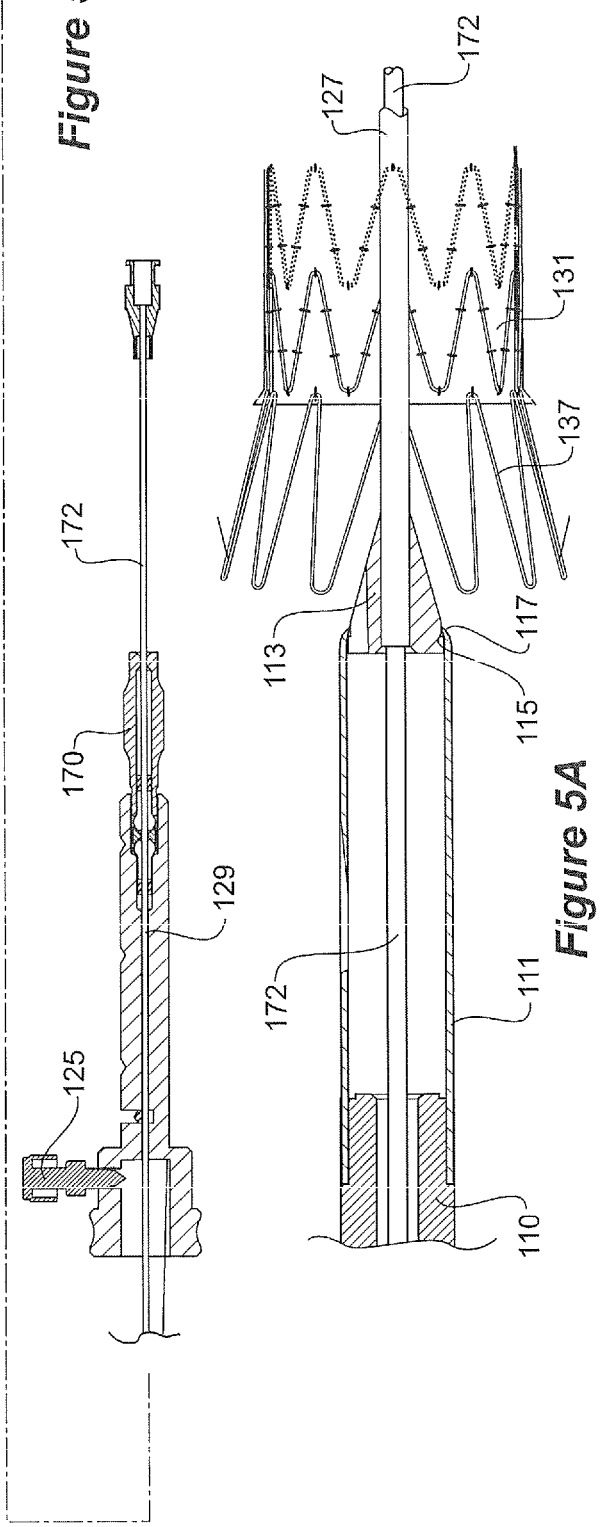
Figure 5
Figure 5A

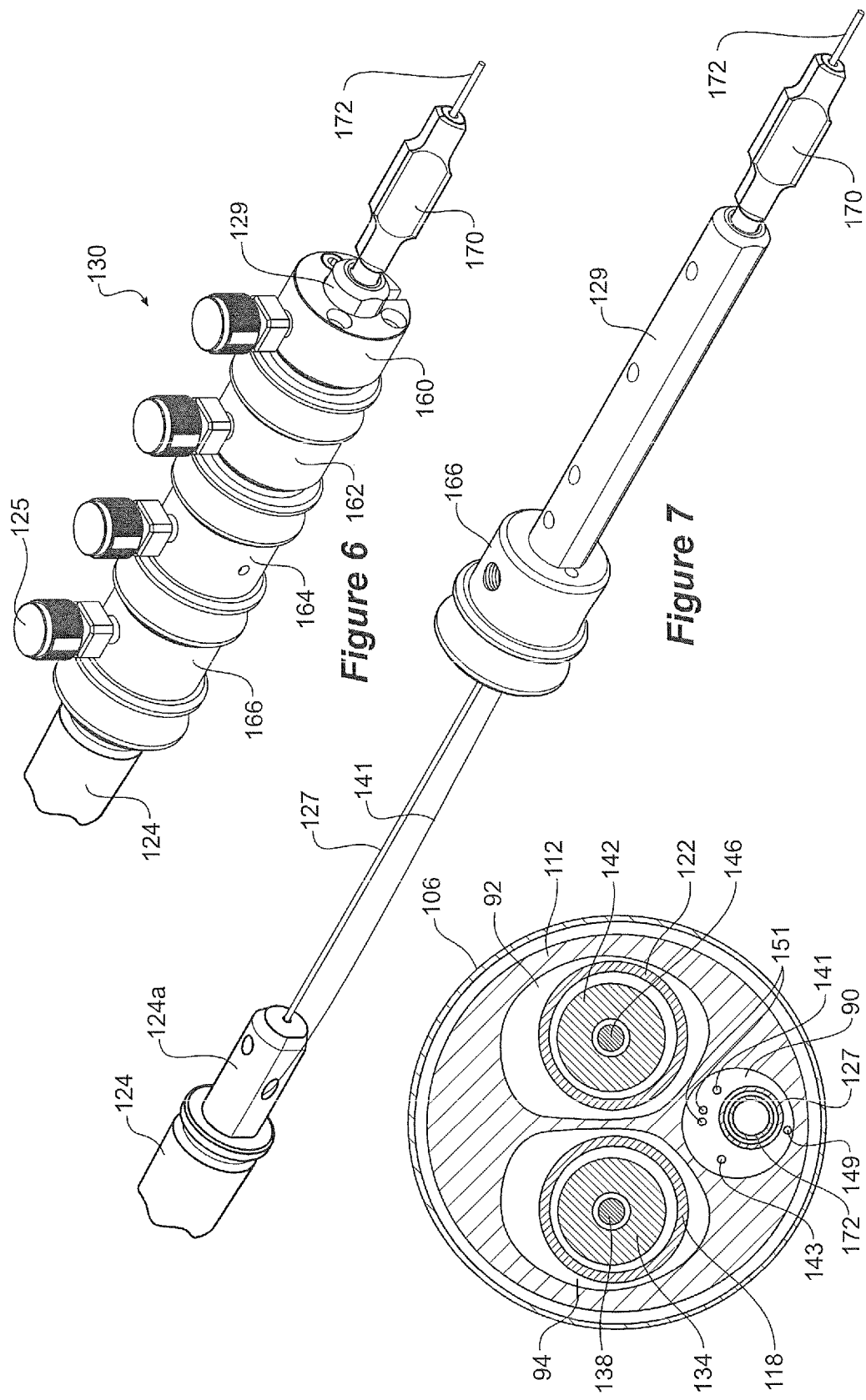

PRE-LOADED MULTIPORT DELIVERY DEVICE

TECHNICAL FIELD

This disclosure relates to a medical device and more particularly to a device for introduction or delivery of a stent graft into the vasculature of a patient.

BACKGROUND

It is known to introduce endovascular stent grafts into the vasculature of a patient to bridge an aneurism or damaged portion of the wall of the vasculature. Problems can occur, however, where the damage to the vasculature includes or is adjacent to a branch vessel from a main artery because occlusion of the branch vessel may cause permanent damage to the patient.

Examples of such branch vessels are the renal and the mesenteric arteries extending from the aorta.

Fenestrations in a stent graft have been proposed to allow access to the branch vessel from a main stent graft but it is often necessary to provide a side branch graft to maintain access into the branch vessel. Catheterization of such a branch vessel from a delivery device through the fenestration enables deployment of a covered stent or uncovered stent into the side vessel. This disclosure provides an improved apparatus for catheterization and deployment of side branch grafts.

In the present application, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first), and the outflow end (that end, from which the fluid exits). When applied to other vessels similar terms such as caudal and cranial should be understood.

Throughout this discussion the term "stent graft" is intended to mean a device, which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the disclosure.

SUMMARY

According to the present application, stent graft delivery device includes two indwelling access sheaths preloaded with a stent graft on the delivery device. The stent graft delivery device comprises a guide wire catheter having a guide wire lumen therethrough; a handle assembly at a distal end of the guide wire catheter, the handle including a multiport manifold; a nose cone dilator at the proximal end of the guide wire catheter; a pusher catheter extending from the manifold towards the nose cone dilator; and a sheath disposed coaxially over the pusher catheter and the stent graft. The pusher catheter comprises a longitudinal pusher lumen therethrough and at least one longitudinal auxiliary lumen of an oblong cross-section. The pusher catheter completely encloses the at least one auxiliary lumen radially. The guide wire catheter extends through the pusher lumen, and the guide wire catheter is able to move longitudinally and rotationally with respect to the pusher catheter. The pusher catheter has a proximal end spaced distally from the nose cone dilator and thereby defines a stent graft retention region between the proximal end of the pusher catheter and the nose cone dilator. The stent graft comprises a stent structure, graft material having a side wall, at least one fenestration in the side wall of graft material, a proximal end, a distal end and a lumen therethrough. The manifold comprises at least one side port and a through bore, the at least one side port extending distally at an angle from the through bore. The pusher catheter further comprises at least one aperture near the distal end of the pusher catheter, and the at least one aperture opens respectively into the at least one auxiliary lumen. The pusher catheter is in communication with the through bore of the manifold such that the at least one aperture communicates respectively with the at least one side port. An indwelling access sheath is disposed within each of the at least one auxiliary lumen and is configured to receive a guide wire. The indwelling access sheath extends through a respective one of the at least one side port, into the manifold from external thereof, into the distal end of the stent graft, through the lumen of the stent graft, and out of the at least one fenestration.

The longitudinal auxiliary lumen may be configured to hold the indwelling access sheath and an additional wire not disposed within the sheath.

The indwelling access sheath may be at least 6 Fr in diameter, where the at least one substantially oblong or oval-shaped longitudinal auxiliary lumen may be configured to hold the indwelling access sheath and an additional catheter not disposed within the sheath. The catheter may be at least 4 Fr in diameter.

Each indwelling access sheath may be configured to receive therethrough a further delivery device comprising a side arm stent.

Each side port has a hemostatic seal assembly and a respective access sheath may extend through the respective hemostatic seal assembly.

The stent graft may have a scallop in the proximal end of the stent graft.

The stent graft delivery device may further comprise a distally facing capsule at a distal end of the nose cone dilator, wherein the proximal end of the stent graft is releasably retained within the distally facing capsule.

The handle assembly may include a proximal handle portion and a distal handle portion, the distal handle portion being movable longitudinally with respect to the proximal handle portion, the guide wire catheter extending through each of the distal handle portion and the proximal handle portion, the nose cone dilator and the distal handle portion being movable longitudinally with respect to the proximal handle portion whereby the nose cone dilator can be retracted or advanced independently of the manifold and pusher catheter.

Each of the auxiliary lumens has a maximum diameter and a minimum diameter. The maximum diameter may extend in a direction enclosing a greater angle with a radial direction of the pusher catheter than the minimum diameter.

The maximum diameter may be greater than the minimum diameter by a factor in a range of 1.4 through 2.

Each indwelling access sheath may be configured to receive therethrough a further delivery device comprising a side arm stent.

Each side port has a hemostatic seal assembly and the respective access sheaths extend through the respective hemostatic seal assembly.

The pusher catheter may include two of the auxiliary lumens, and the manifold may include at least 3 side ports, two of which being jointly in communication with a common one of the two auxiliary lumens.

The pusher catheter may two of the auxiliary lumens and the manifold may include at least four side ports, two of which being jointly in communication with a common one of two auxiliary lumens.

According to a further aspect of the present disclosure, a method of placing a fenestrated stent graft in a body vessel at a treatment site comprises the following steps of introducing a proximal end of a stent graft delivery device as described above into a body vessel and advancing the delivery device to the treatment site; partially withdrawing the sheath from the stent graft to expose the indwelling access sheath; advancing a guide wire through each of the at least one access sheath, out of the at least one fenestration and into a respective target branch vessel branching from the body vessel; advancing the at least one access sheath to the target branch vessel; releasing the proximal end of the stent graft from the distally facing capsule; advancing a side arm stent through each of the at least one indwelling access sheath and at least partially out of the respective fenestration and into the respective target branch vessel, the side arm stent having a proximal end and a distal end; expanding each of the at least one side arm within the target vessel with a balloon; flaring the proximal end of the side arm stent within the lumen of the stent graft.

The method may include an additional catheter within each auxiliary lumen and additionally or alternatively an additional wire within each auxiliary lumen.

Further details and benefits of the present disclosure are described by way of the accompanying drawings. The drawings are provided for purely illustrative purposes and are not intended to limit the scope of the present invention.

BRIEF DESCRIPTION OF THE DRAWINGS

FIG. 2 shows a longitudinal cross sectional view of the embodiment of a stent graft delivery device of FIG. 1 according the present disclosure;

FIG. 2A shows the embodiment shown in FIG. 1 and in particular a detail of a part of the distal handle portion;

FIG. 2B shows the embodiment shown in FIG. 1 and in particular a detail of a part of the nose cone dilator and capsule with the distal retrieval taper;

FIG. 3 shows the embodiment shown in FIG. 1 in a first partially activated condition;

FIG. 5 shows the embodiment shown in FIG. 41 in longitudinal cross section;

FIG. 5A shows the embodiment shown in FIG. 1 and in particular a detail of a part of the nose cone dilator and capsule with the distal retrieval taper in its distal position;

FIG. 6 shows a perspective view of part of the handle of the embodiment shown in FIG. 1;

FIG. 7 shows the view of FIG. 6 in an activated condition;

FIG. 8 shows one example of a transverse cross sectional view of the pusher catheter portion of the embodiment shown in FIG. 1 along the line 8-8';

DETAILED DESCRIPTION OF THE DRAWINGS

Figure 1:
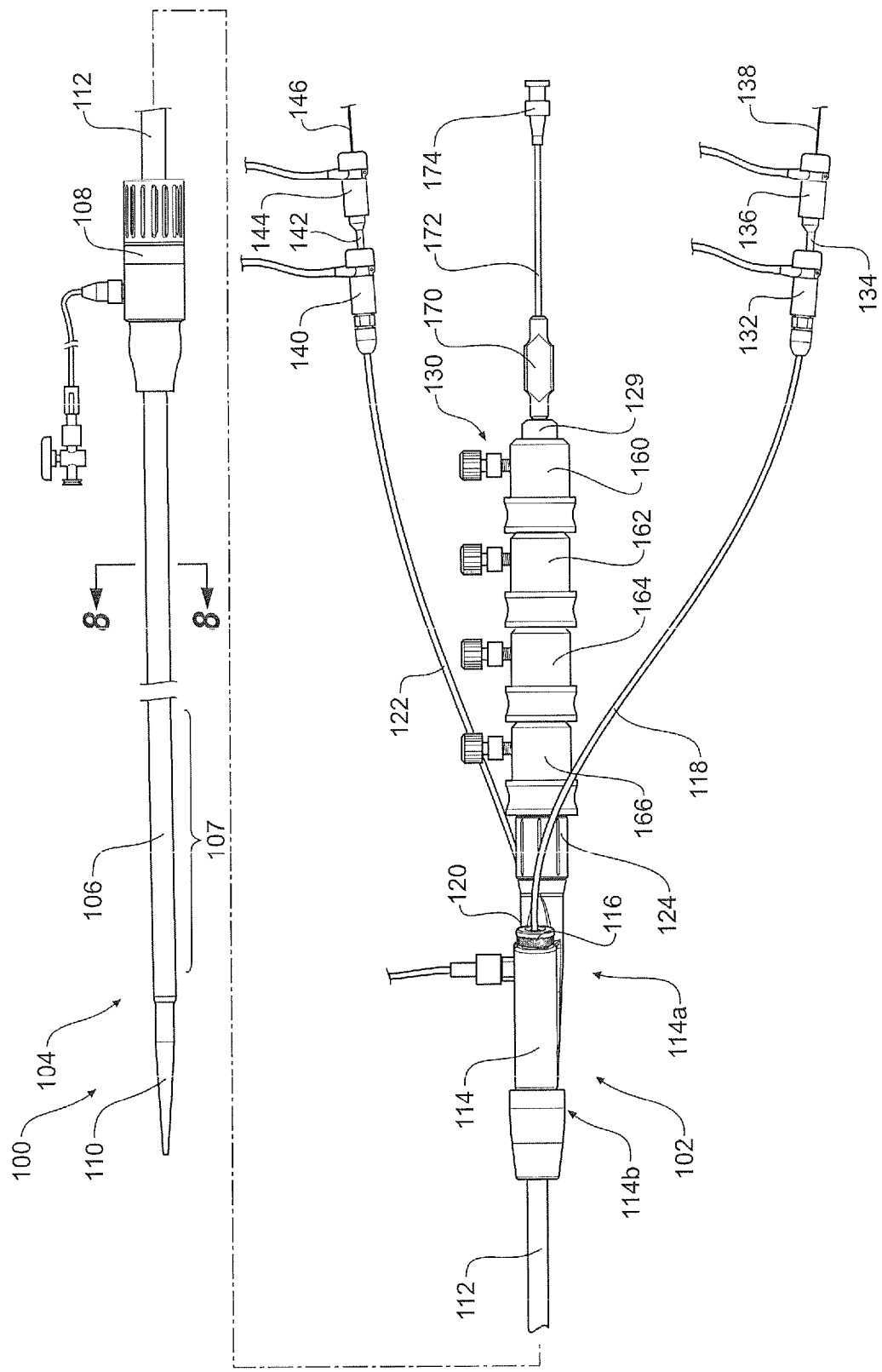
FIG. 1 shows a first embodiment of a pre-loaded stent graft delivery device according to the present disclosure.

The drawings, FIGS. 1 to 11D show a first embodiment of a pre-loaded delivery device according to the present disclosure.

The delivery device 100 comprises a handle and manifold assembly 102 and introduction portion 104 intended to be deployed into the patient by the known Seldinger method. More specifically the introduction section 104 includes a sheath 106 extending from a sheath hub 108 to a nose cone dilator 110. A stent graft 131 is retained within the outer sheath 106 in the region 107 just distal of the nose cone dilator 110.

The sheath hub 108 including a hemostatic seal is positioned over a pusher catheter 112, which extends from and is connected into a manifold 114 as is discussed in more detail below. The manifold 114 has a proximal end 114b, into which the pusher catheter 112 is affixed, and a distal end 114a with two access ports 116, 120. Access port 116, which has a hemostatic seal, accommodates a first access sheath 118. Access port 120, which also has a hemostatic seal, accommodates a second access sheath 122. At the rear end 114a of the manifold, a handle assembly 130 is connected. The handle assembly 130 includes trigger wire release mechanisms and can be separated into two parts is as discussed below.

The access sheath 118 extends to a hemostatic seal 132, through which extends a dilator 134. On the dilator 134 is a dilator hemostatic seal 136, through which extends an indwelling guide wire 138.

The access sheath 122 extends to a hemostatic seal 140, through which extends a dilator 142. On the dilator 142 is a dilator hemostatic seal 144, through which extends an indwelling guide wire 146.

The handle assembly 130 includes a proximal handle portion 124, which is affixed to the rear of the manifold 114. The handle assembly 130 also includes a distal handle portion 129. The distal handle portion 129 has a proximal recess 129a, which fits over a distal extension 124a of the proximal handle portion 124 and a locking screw 125 releasably locks the two handle portions together.

The distal handle portion 129 of the handle assembly 130 includes trigger wire release mechanisms releasably mounted onto it from its distal end as follows. Trigger wire release 160 is for the release of the stabilization retention of indwelling guide wires as will be discussed below. Trigger wire release 162 is for diameter reducing ties as will be discussed below. Trigger wire release 164 is for a retention trigger wire for the exposed stent in the capsule as will be discussed below. Trigger wire release mechanism 166 is for the distal end of the graft as will be discussed below. Trigger wire release mechanism 166 is also part of the distal portion of the handle 129 and moves with it.

A pin vice 170 is at the rear of the handle assembly 130 and the guide wire catheter 172 for the delivery device extends through the pin vice 170 and is locked and can be released for movement with respect to the distal portion of the handle 130 by the pin vice. The guide wire catheter 172 terminates in a syringe point 174 to enable flushing liquid and radiopaque medium to be deployed through the delivery device.

The introduction portion 104 of the stent graft delivery device 100 has the nose cone dilator 110 and at the distal end of the nose cone dilator 110 is a distally opening capsule 111 for the receipt of an exposed stent 137 of a stent graft 131. The capsule 111 has a slightly in-turned distal end 117 (see FIGS. 4A and 5A). This has two purposes, a first is to assist with engagement of the sheath 106 of the delivery device when the nose cone dilator 110 is retracted into the sheath 106 and a second is to prevent complete withdrawal of a distal retrieval taper device 113 from the capsule as will be discussed below. The guide wire catheter 172 passes through and is fastened to the nose cone dilator 110 at its proximal end and passes through the handle assembly 130 of the delivery device. The pin vice arrangement 170 at the distal end of the distal handle portion 129 locks movement of the guide wire catheter 172 with respect to the distal portion of the handle 129 and can be loosened to allow relative motion between these components as discussed below.

The stent graft 131 shown in FIG. 2 for instance comprises a tubular body of a biocompatible graft material such as Dacron (polyethylene terephthalate), expanded PTFE or Thoralon, a polyurethane material. The stent graft is supported by self expanding stents (not shown for clarity). A proximally extending exposed stent 137 assists with providing infra-renal fixation of the deployed stent graft. The stent graft has two fenestrations 147, which are provided to give access to the renal arteries. The stent graft is retained on the delivery device by proximal retention of the exposed stent 137 into the capsule 111 of the delivery device and distally by a trigger wire retention 145 as will be discussed in detail below. Diameter reducing ties can be used to hold the stent graft in a diameter reduced condition during the initial catheterization of a side branch because it may still be necessary to move the stent graft proximally or distally or rotate it. In the diameter reduced condition this is still possible whereas when released to full diameter this may not be possible.

As can be seen particularly in FIGS. 5 and 5A the distal retrieval taper device 113 fits coaxially around the guide wire catheter 172 and can move longitudinally along the guide wire catheter. A retrieval catheter 127 is mounted coaxially around the guide wire catheter 172 and can move longitudinally along the guide wire catheter. At its proximal end the retrieval catheter 127 is joined to the distal retrieval taper device 113 and at its distal end the retrieval catheter 127 is joined to the distal handle portion 129 at 133 by a suitable adhesive 135. For this purpose apertures are provided into the handle and adhesive is applied through these apertures. FIG. 2A shows detail of the mounting of the retrieval catheter into the distal handle portion.

The distal retrieval taper device is shown in detail in FIGS. 5 and 5A. The distal retrieval taper device 113 has an enlarged shoulder 115 at its proximal end. The shoulder is sized so that it is of greater diameter than the smallest part of the in-turned distal end 117 of the capsule 111. By this arrangement the distal retrieval taper device can move through the capsule but cannot be fully removed from the capsule. The retrieval catheter 127 is coaxial with the guide wire catheter 172. At its proximal end the retrieval catheter 127 is affixed to the distal retrieval taper device and at its distal end the retrieval catheter 127 is affixed to the distal handle portion 129 as shown in FIG. 2A. This means that movement of the guide wire catheter 172 proximally with respect to the distal handle portion 129, after release of the pin vice 170 will move the nose cone dilator 110 and capsule 111 with respect to the distal retrieval taper device with the effect that the distal retrieval taper extends from the capsule thereby providing a smooth tapered surface for retrieval of the nose cone dilator through the stent graft. Locking of the pin vice after the distal retrieval taper 113 has been moved to the distal end of the capsule 111 ensures that all of the distal retrieval taper, the capsule, the nose cone dilator and the distal handle portion all move together.

By this arrangement the nose cone dilator can be moved to a distal position with respect to fenestrations in the stent graft so that the nose cone dilator and distally opening capsule does not interfere with the deployment of side branch covered or uncovered stent grafts through such fenestrations nor does any subsequent retraction of the nose cone dilator interfere with the deployed of side branch side branch covered or uncovered stent grafts.

As can be seen particularly in FIG. 8, which is a transverse cross section along the line 8-8' as shown in FIG. 1, the pusher catheter 112 is surrounded by the sheath 106. The pusher catheter has three longitudinally extending lumens. A first lumen is the guide wire lumen 90 and this lumen is off-set from the center of the pusher catheter to allow for two auxiliary lumens 92 and 94. The guide wire lumen 90 has passing through it the guide wire catheter 172 and coaxially around that the retrieval catheter 127. Also in the guide wire lumen are the trigger wires for the diameter reducing ties 149, the top capsule 143, the distal retention 141 and the auxiliary guide wire stabilization 151. The auxiliary lumen 94 has the access sheath 118 extending through it and the dilator 134 and guide wire 138 extend through the access sheath 118. The auxiliary lumen 92 has the access sheath 122 extending through it and the dilator 142 and guide wire 146 extend through the access sheath 122. While the guide wire limen 90 has a generally circular cross-sectional shape, the two auxiliary lumens 92 and 94 are non-circular in cross-section. As shown, the auxiliary lumens 92 and 94 have a greater dimension in a tangential direction than in a radial direction of the pusher catheter 112. For example, the dimensions of the auxiliary lumens 92 and 94 in the tangential direction of the pusher catheter 112 may be greater than the radial dimension by a factor 1.3 to 2. Further details of the cross-sectional shapes of the auxiliary lumens 92 and 94 will be discussed below in connection with FIG. 17.

Figure 9:
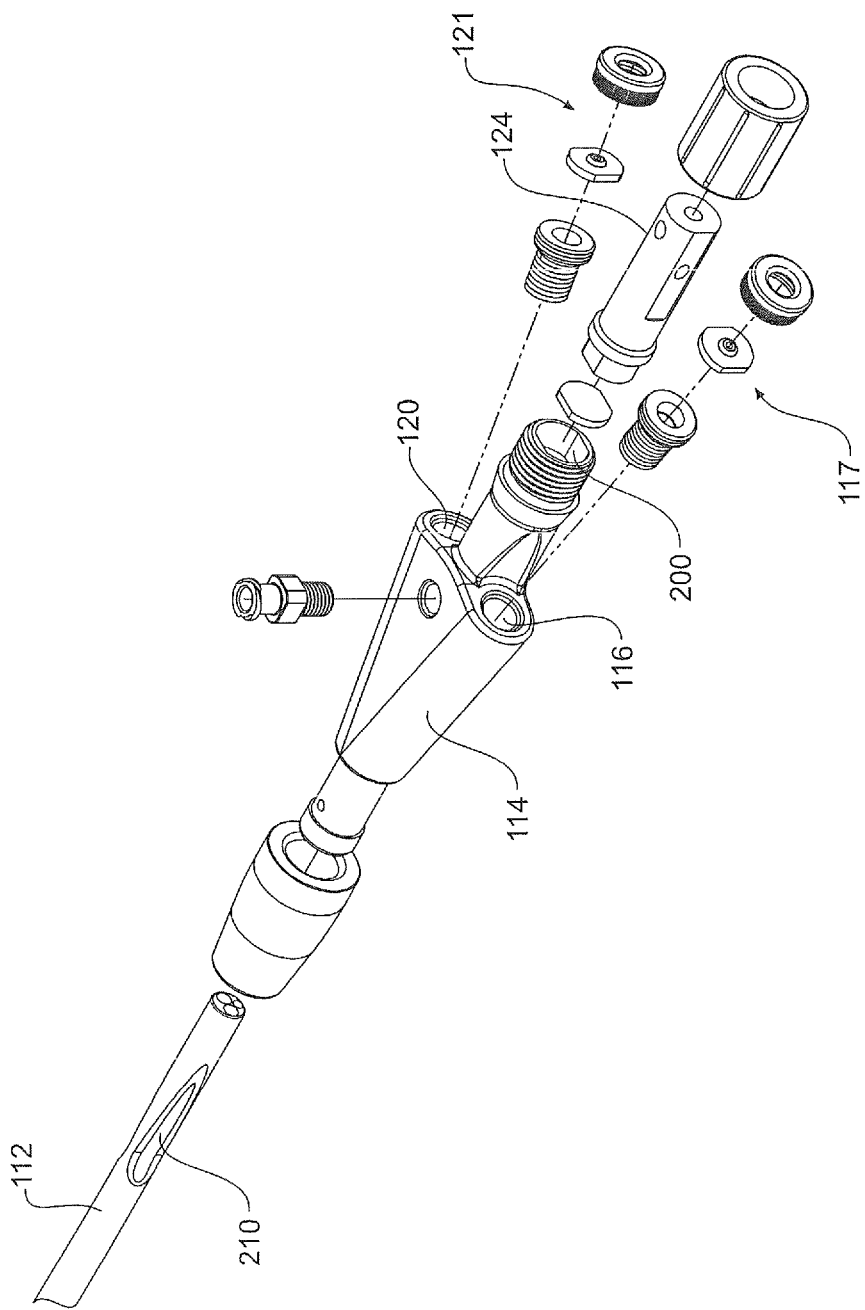
FIG. 9 shows an exploded view of a manifold of an embodiment of the present disclosure.
Figure 10A:
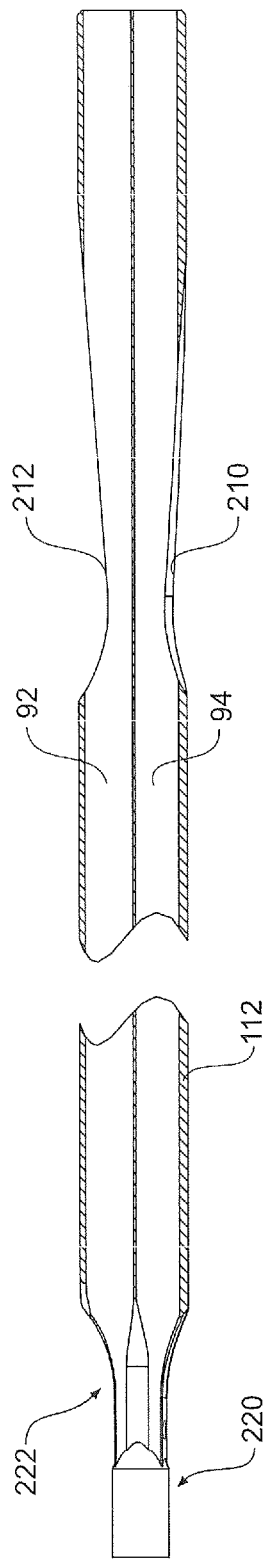
FIGS. 10A, 10B, 10C, and 10D show various views of the pusher catheter of an embodiment of the present disclosure.
Figure 10B:
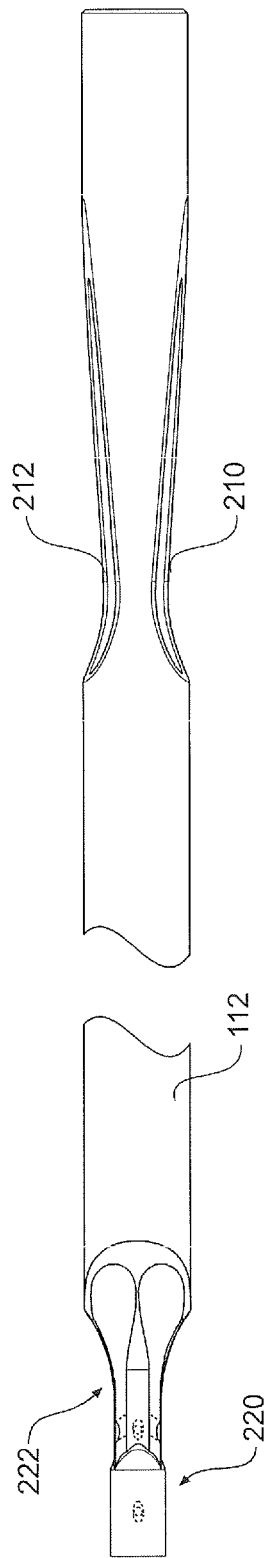
Figure 10C:
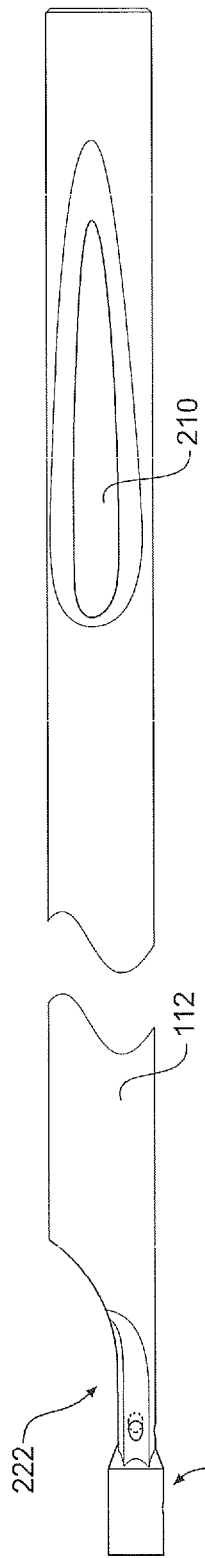
Figure 10D:
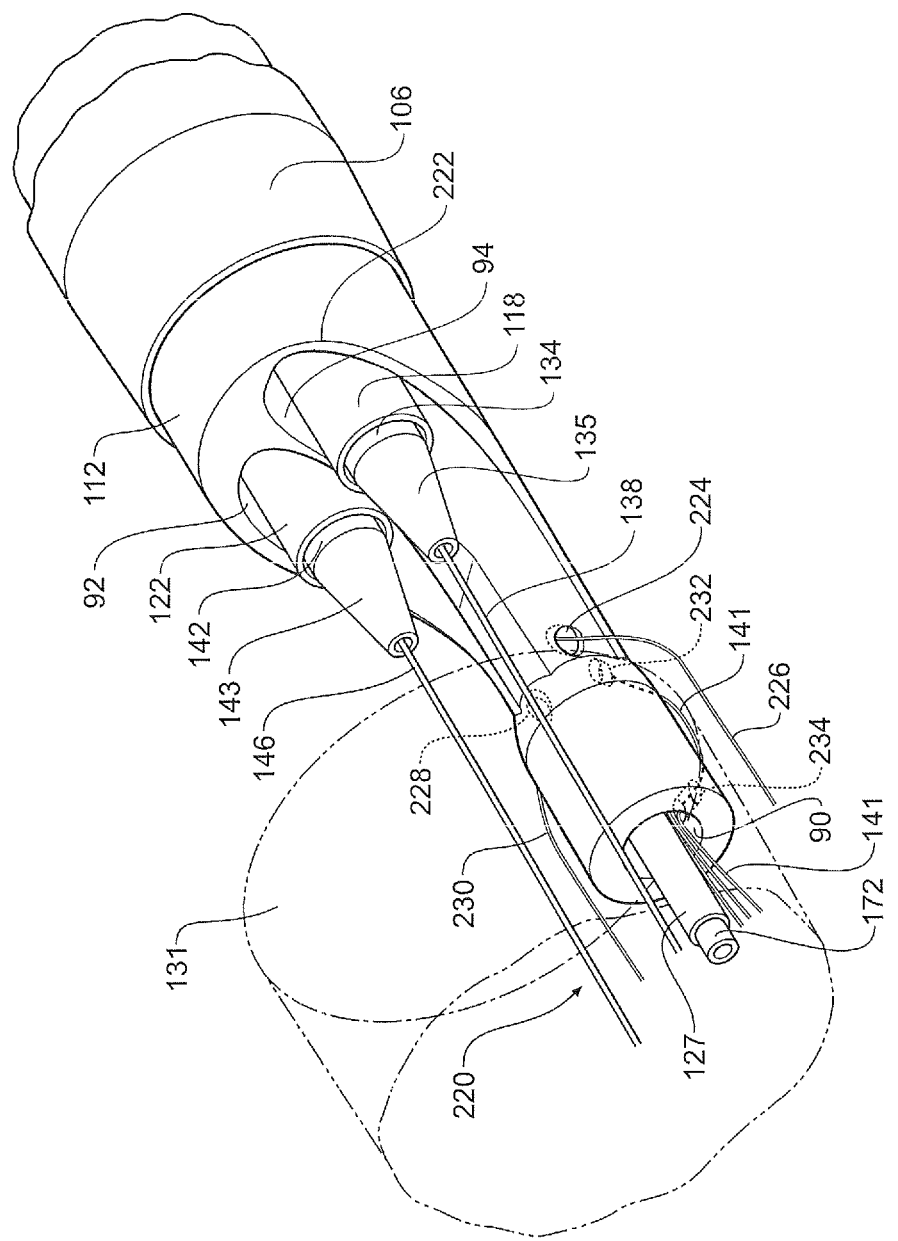
Figure 11:
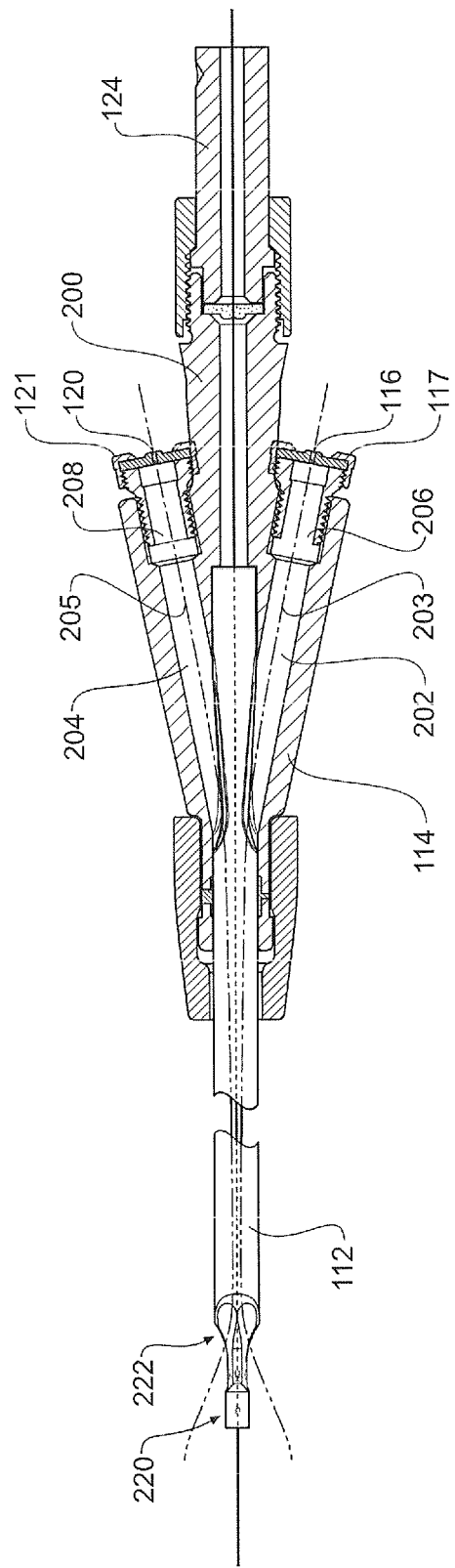
FIG. 11 shows a cross sectional view of the assembly of a manifold and pusher catheter according to the present disclosure.

The manifold 114 and pusher catheter is shown in more detail in FIGS. 9 to 11.

The manifold 114 has a through bore 200 and angled side ports 202 and 204. The pusher catheter has three lumens as shown on FIG. 8, the guide wire lumen 90 and this lumen is off-set from the center of the pusher catheter to allow for two auxiliary lumens 94 and 92. As can be seen in FIGS. 10A to 10C the pusher catheter 112 has two side apertures 210 and 212, which open from the side of the pusher catheter into the respective lumens 92 and 94. These side apertures are elongate and tapered towards the distal end. When the pusher catheter is pushed into the through bore 200 of the manifold 114 the side apertures in the pusher catheter align with the respective angled side ports 202 and 204 thereby providing an uninterrupted lumen from the access port 116 for the first access sheath 118 into the pusher lumen 94 along the dotted line 203 and from access port 120 for a second access sheath 122 into the pusher lumen 92 along the dotted line 205.

As can be best seen in FIG. 10A to 10D, at the proximal end of the pusher catheter is an attachment boss 220 and a scalloped end 222 to provide exit ports for the two auxiliary lumens 92 and 94. The guide wire lumen 90 opens out at the proximal end of the attachment boss 220 and to each side of the attachment boss there are apertures for trigger wires. Aperture 224 is for trigger wire 226, which is used for the diameter reducing ties on one side of the stent graft 131. A corresponding aperture 228 and the other side of the attachment boss 220 is for the trigger wire 230 for the other side of the stent graft 131.

Trigger wire 141 extends out of aperture 232 in the attachment boss 220 and engages into the stent graft 131 before re-entering the attachment boss at aperture 234 and exiting the guide wire lumen 90 at the proximal end of the pusher catheter 112.

Extending out of the two auxiliary lumens 92 and 94 are the auxiliary catheters 122 and 118 respectively. From the proximal ends of the respective auxiliary catheters 118 and 122 extend dilators 134 and 142. The auxiliary guide wires 138 and 146 extend through the dilators.

Figure 12:
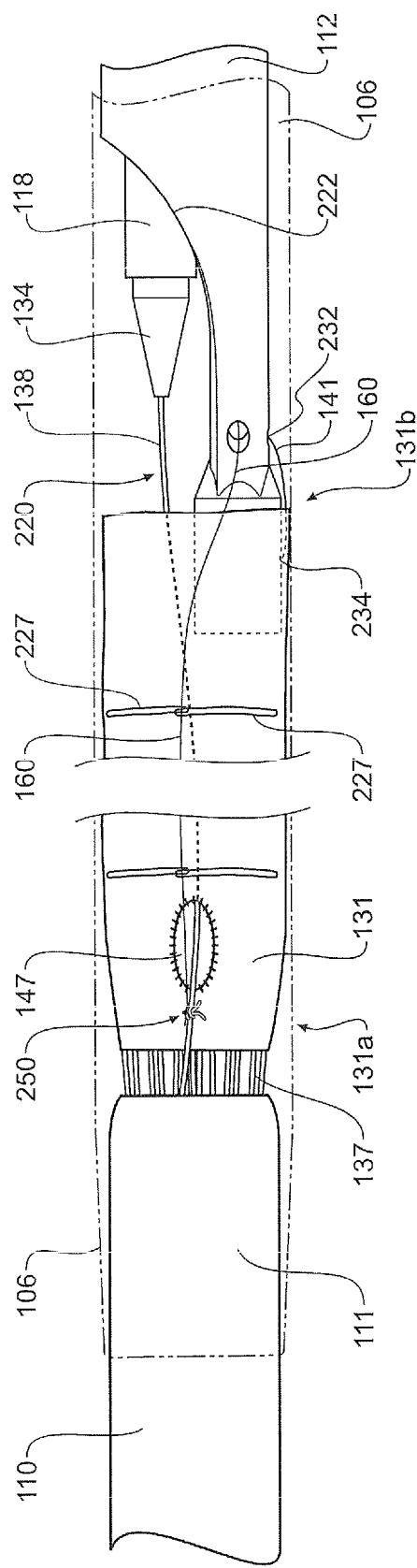
FIG. 12 shows a schematic detailed side view of the stent graft retained on the delivery device.

FIG. 12 shows detail of the stent graft 131 and its retention system in the region 107 as shown in FIG. 1. In particular there is detail shown of the distal attachment, the diameter reducing ties and the proximal retention.

The stent graft 131 is retained within the sheath 106 and concentrically around the guide wire catheter 172 and retrieval catheter 127. The stent graft has a fenestration 147 towards its proximal end. In use the stent graft is deployed so that the fenestration is substantially aligned with a renal artery and it is intended to catheterize the renal artery through the fenestration to deploy a covered or uncovered side branch stent or stent graft into the renal artery. The stent graft has a proximally extending exposed stent 137 at is proximal end 131a. In its ready to deploy condition the proximally extending exposed stent 137 is received into the capsule 111 at the distal end of the nose cone dilator 110. At its distal end 131b the stent graft is retained to the attachment boss 220 at the proximal end of the pusher catheter 112. Trigger wire 141 engages the distal end of the stent graft. Trigger wire 141 extends out of aperture 232 in the attachment boss 220 and engages into the stent graft 131 before re-entering the attachment boss through aperture 234 into the guide wire lumen 90 and exiting the guide wire lumen 90 at the proximal end of the pusher catheter 112. At its distal end the trigger wire 141 is attached to the trigger wire release mechanism 166. Trigger wire release mechanism 166 is also part of the distal portion of the handle 129.

The stent graft 131 has diameter reducing tie arrangements to retain it in a partially diameter reduced condition even after the sheath 106 has been retracted during deployment. The diameter reducing tie arrangement are on each side of the stent graft and comprise a trigger wire 160 stitched along the graft material on either side of the stent graft and loops of filament such as suture thread 227 engaged around the trigger wire and a portion of the graft material part way around the stent graft and then drawn tight.

Figure 13:
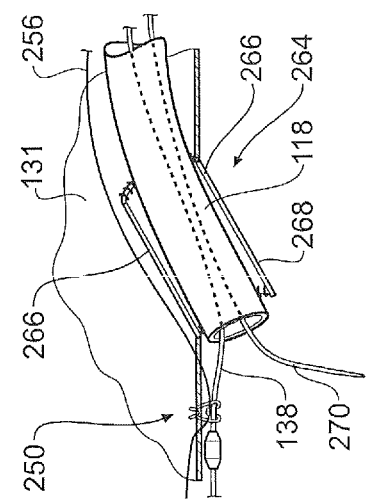
FIG. 13 shows a method of releasable retention of the indwelling guide wire.

FIG. 13 shows detail of the retention system 250, by which the guide wires 138 (for instance) is stabilized proximally of the fenestration 147 (for instance). The guide wire 138 has a protrusion 252, which can be fastened with respect to the guide wire by solder, crimping, welding or gluing. A suture thread 254 is looped 254b around the guide wire 138 distally of the protrusion 252 and around a release wire 256, which is stitched through the material of the stent graft 131, and then the suture thread 254 is sewn at 254a into the material of the stent graft 131. When the release wire 256 is retracted the loop 254b of the suture thread 254 is released and the guide wire 138 can be retracted. In the meantime the retention system stabilizes the guide wire.

Figure 14:
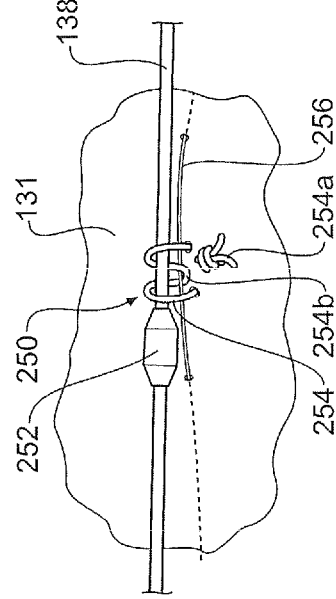
FIGS. 14 and 15 show two embodiments of fenestrations suitable for the present disclosure.

FIG. 14 shows a cross section of a simple fenestration in cross section with the stabilized auxiliary guide wire extending through it. In this embodiment the fenestration 260 is reinforced with a ring of resilient wire such as Nitinol wire. The auxiliary guide wire 138 passes through the fenestration and is restrained just proximal of the fenestration using a retention system 250 as shown in FIG. 13.

Figure 15:
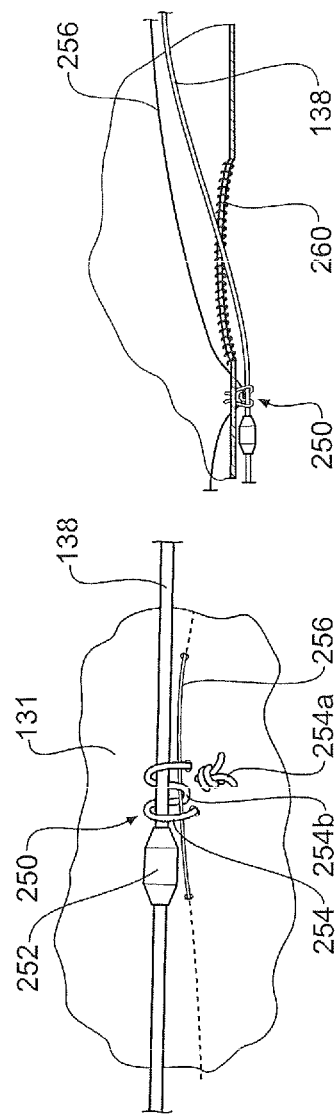

FIG. 15 shows a cross section of an alternative fenestration arrangement incorporating a low profile side arm with the stabilized auxiliary guide wire extending through it. In this embodiment the fenestration 264 is in the form of a low profile side arm 264. The low profile side arm 264 has an inner portion 266, which extends within the tubular body of the stent graft, and an outer portion 268, which extends outside of the tubular body of the stent graft and is stitched into the periphery of the fenestration. The stitching extends circumferentially and diagonally from one end of the low profile side arm to the other.

In FIG. 15 the fenestration is shown at the stage of deployment, at which the first access sheath 118 has been advanced over the auxiliary guide wire 138 until it just extends out of the low profile side arm 264. The auxiliary guide wire 138 passes through the fenestration and is restrained just proximal of the fenestration using a retention system 250 as shown in FIG. 13 and this stabilizes the access sheath 118 while catheterization of a side branch artery is occurring. The dilator has been retracted and another guide wire 270 has been deployed through the access sheath 118 and this guide wire be used to catheterize of the side branch artery.

Figure 16:
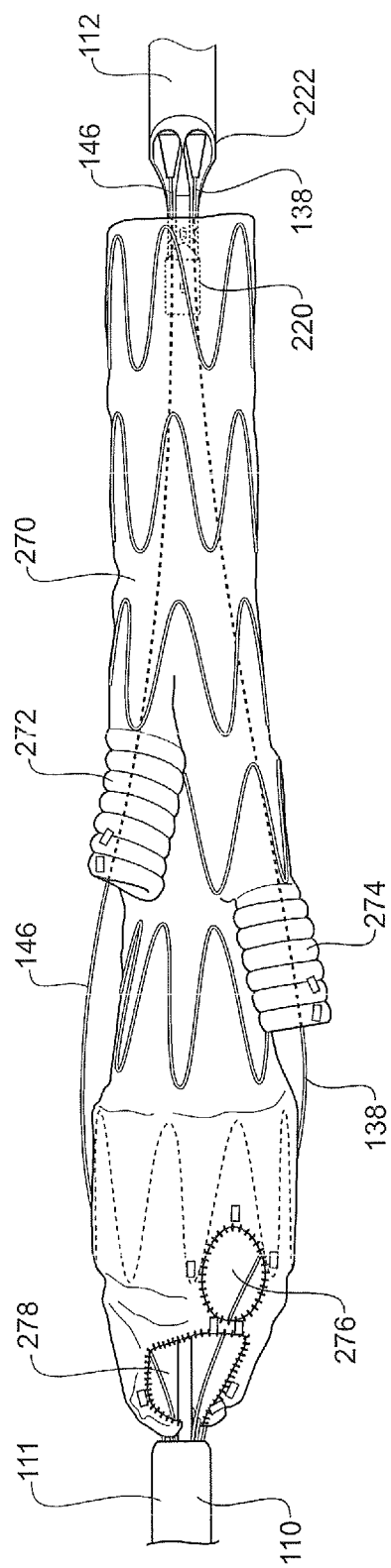
FIG. 16 shows an alternative embodiment of stent graft on a delivery device of the present disclosure.

FIG. 16 shows an alternative embodiment of stent graft on a delivery device of the present disclosure. In this embodiment the stent graft 270 has two high flexibility side arms 272 and 274, which are intended for connection to respective renal arteries, a fenestration 276 for the celiac artery and a scalloped proximal end 278 for the superior mesenteric artery. The auxiliary guide wires 138 and 146 extend from the pusher catheter 112 within the stent graft 270 and pass out through the respective two high flexibility side arms 274 and 272 and are then stitched into the graft material to extend into capsule 111 on the nose cone dilator 110. The stitching into the stent graft material proximally of the open ends of the two high flexibility side arms 272 and 274 assists in stabilization of the side arms during the catheterization of the renal arteries.

In the embodiment of the delivery device shown in FIGS. 1 to 14 the following components are present:

1/ Guide wire catheter 172 extending from a handle 130 to a nose cone dilator 110.

2/ Handle 130 comprising a proximal handle portion 124 and a distal handle portion 129. The handle has:
 a) Trigger wire release for top cap 164,
 b) Trigger wire release for diameter reducing ties 162
 c) Trigger wire release for stabilization retention of indwelling guide wire 160 on the distal portion of handle with respective trigger wires.
 d) Trigger wire release for distal end of the stent graft on distal handle portion with respective trigger wire 141.

5/ Pusher catheter 112 with lumens for access sheath 92, 94 and guide wire catheter 90 joined to proximal handle portion 124 via manifold 114.

6/ Sheath 106 with sheath hub 108 on pusher catheter 112.

7/ Nose cone dilator 110 with a distally opening top capsule 111.

8/ Indwelling guide wires 138, 146 through fenestrations 147 in stent graft 131 and into top capsule 111. Indwelling guide wires go through access sheaths 118, 122.

9/ Stabilization retention system 250 of indwelling guide wires 138 and 146 proximally of fenestration 147.

10/ Distal retrieval taper 113 in top capsule 111 coaxial with guide wire catheter 172 and a retrieval catheter 127 extending from retrieval taper 113 to and fixed to distal portion of handle 129.

11/ Access sheaths 118 and 122 having dilators 134 and 142 respectively within them and the dilators having dilator tips 135 and 143;

12/ Stent graft 131 with:
 e) Proximally extending exposed stent 137 received in top capsule 111 and a top cap trigger wire 143 retention
 f) Distal retention at 145
 g) Fenestrations for renal arteries, for instance 147
 h) Radiopaque markers (not shown)
 i) Diameter reducing ties 227 and trigger wire 160.

Introduction steps are as follows:

(a) Position the introduction part 104 of the delivery device 100 into the aorta correctly taking into account N—S position as well as rotational position with respect to target vessels and fenestrations on the stent graft 131 using markers on stent graft body. At this stage the delivery device is as shown in FIGS. 1 and 2.

(b) Withdraw the outer sheath 106 of the delivery device while continuing to check position until the distal end of the stent graft opens. At this stage the distal end of the stent graft is still retained by distal fixation, the proximal end is retained by the exposed stent retained in top capsule of the delivery device and the expansion of the stent graft is restricted by the diameter reducing ties. This stage is shown in part in FIG. 3A.

(c) Advance the access sheaths 118, 122 (left and right) on their respective indwelling guide wires 138 146 through the lumen of stent graft 131 to or through the fenestration 147 (at this stage the top capsule still retains the exposed stent and the indwelling guide wires).

(d) Position the first access sheath at the opening of the fenestration.

(e) Remove the dilator 134 of the first access sheath.

(f) Advance an additional catheter and additional guide wire (4-5 Fr) through the first access sheath and into the target vessel (e.g. renal artery). The additional catheter may have a crooked or hockey stick tip to facilitate access.

(g) Remove the guide wire from the additional catheter and re-insert a stiffer wire into the target vessel.

(h) Release the stabilization retention system 250 of indwelling guide wires 138 via the trigger wire release 160.

(i) Retrieve the indwelling wire guide from the top cap and pull it out completely.

(j) Remove the additional catheter and replace the access sheath dilator and dilator catheter over the stiffer wire in the target vessel and advance the access sheath over the stiffer wire into the target vessel. Withdraw the access sheath dilator.

(k) Repeat steps (d) to (j) for the other of the target vessels.

(l) Advance covered stents through each of the access sheaths into the target vessels but do not release.

(m) Release the diameter reducing ties by releasing and withdrawing trigger wire release 162.

(n) Release the top capsule 111 by removing the locking trigger wire 143 via trigger wire release 164, releasing the pin vice 170 and advancing the top capsule on the guide wire catheter and release the top exposed stent. At the same time the distally facing capsule moves proximally over the distal retrieval taper device to allow the distal retrieval taper device to extend from the distal end of the capsule. This stage is shown in FIG. 3.

(o) Tighten the pin vice 170.

Figure 4:
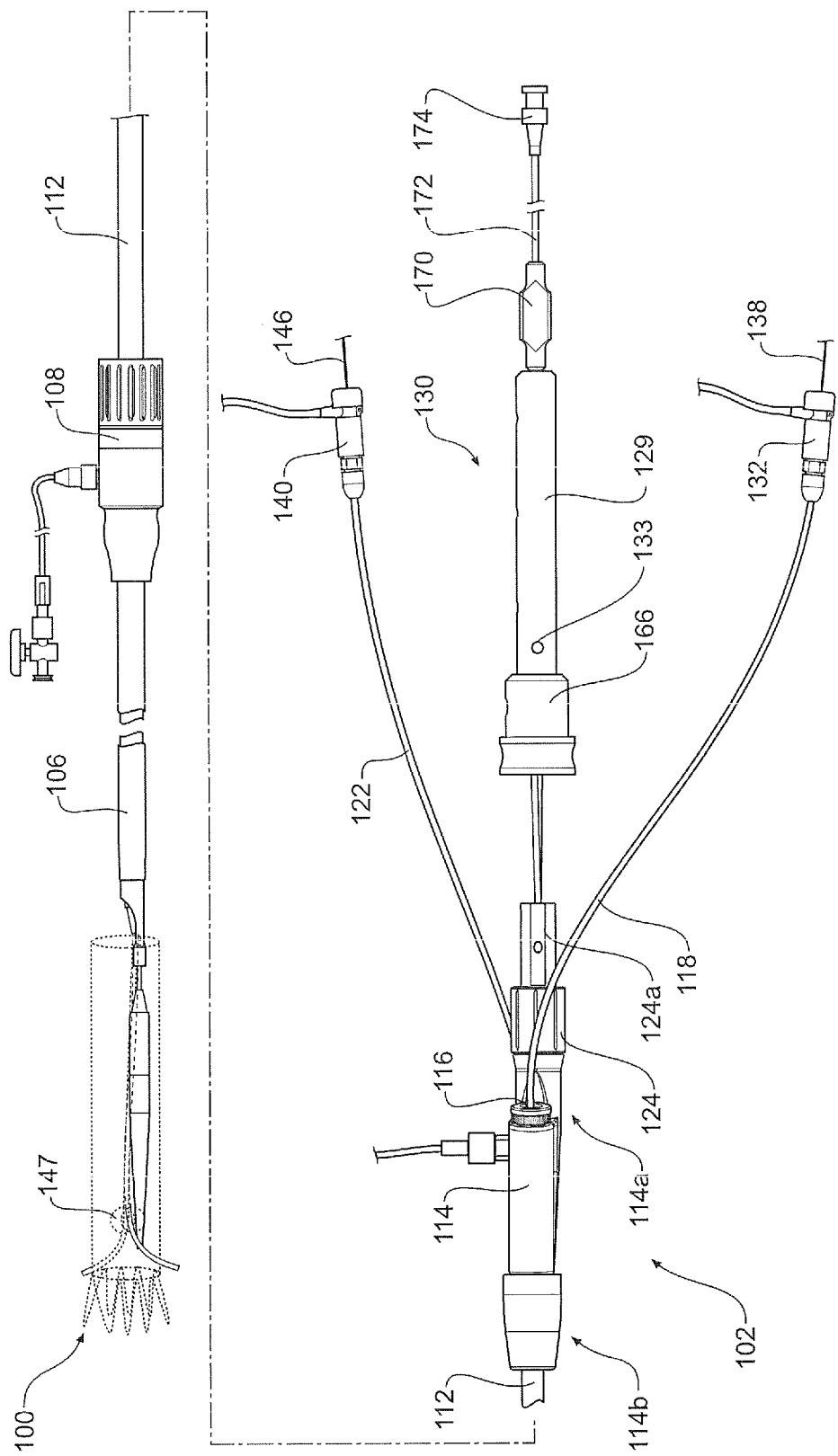
FIG. 4 shows the embodiment shown in FIG. 1 in a further partially activated condition.

(p) Retract the nose cone dilator, top cap and distal retrieval taper past the fenestration by removing the locking screw 125 of the distal handle portion and retracting distal portion of handle. This also releases the distal attachment via trigger wire 141 connected to trigger wire release 166. This stage is shown in FIGS. 4, 5 and 7.

(q) One at a time, withdraw the access sheaths from the target vessels and deploy covered stents between the fenestrations and target vessels and balloon expand if necessary including flaring within the main stent graft.

(r) Remove both access sheaths and also the guide wires from the target vessels and withdraw them from the system.

(s) Retract the nose cone dilator, top cap and distal retrieval taper to the sheath 106.

(t) Withdraw the entire assembly or leave the outer sheath in place for further deployments. Further deployment may include a bifurcated distal component.

Figure 17:
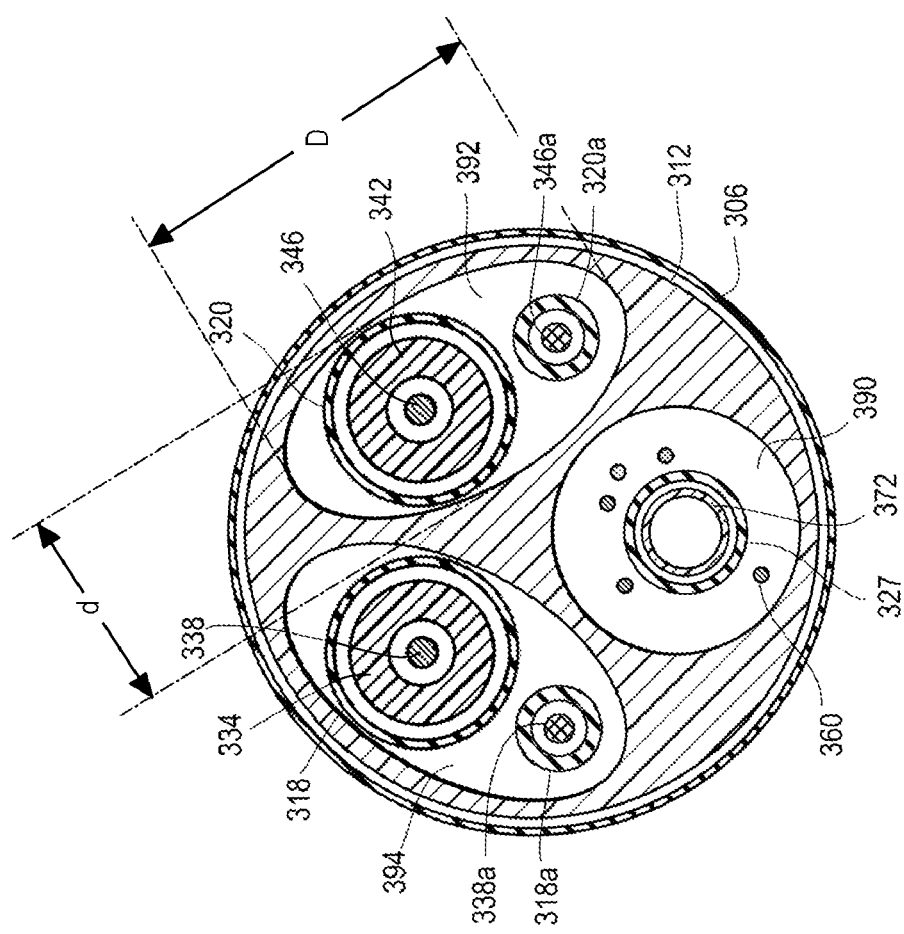
FIG. 17 shows an alternative example of a transverse cross sectional view of the pusher catheter portion of the embodiment shown in FIG. 1 along the line 8-8'.

FIG. 17 shows an alternative example of a transverse cross sectional view of the pusher catheter portion of the embodiment shown in FIG. 1 along the line 8-8'. FIG. 17 is not drawn to scale.

In the example shown in FIG. 17, a pusher catheter 312 is surrounded by a sheath 306. The pusher catheter 312 has three longitudinally extending lumens: a guide wire lumen 390 and two auxiliary lumens 392 and 394.

The guide wire lumen 390 is a generally circular-shaped lumen, which may be off-set from the center of the pusher catheter 312 to allow for two auxiliary lumens 392 and 394. The guide wire lumen 390 may have a guide wire catheter 372 disposed therein. A retrieval catheter 327 may be disposed therein that is coaxially around the guide wire catheter 372. The guide wire lumen 390 may also have disposed in it one or more trigger wires 360. These trigger wires 360 may be used as release mechanisms in conjunction with any delivery component. In one example, trigger wires 360 may be used with diameter reducing ties, the top capsule, distal retention, and auxiliary guide wire stabilization. In one example there may be up to three trigger wires at each end: two diameter reducing ties and one for distal retention.

The two auxiliary lumens 392 and 394 may have generally oval or oblong cross-sections and are offset from the center of the pusher catheter 312 to allow for the guide wire lumen 390.

As described below, the oblong cross-section of the auxiliary lumens 392 and 394 allows space for an additional sheath and wire, or possibly a catheter. Because these oblong auxiliary lumens 392 and 394 have non-circular cross-sections, each of these oblong auxiliary lumens 392 and 394 has two different diameters, a maximum diameter D in one direction and a minimum diameter d typically perpendicular thereto. It should be appreciated, however, that irregular cross-sectional shapes of the auxiliary lumens may result in minimum diameters d that are not exactly perpendicular to the maximum diameters D. In general, for packaging reasons, the minimum diameter d encloses a smaller angle with a radial direction than the maximum diameter D. In this context, the term "diameter" refers to the greatest distance between opposing wall locations in a given direction. Thus, while short distances may be present between arbitrary wall locations, these short distances are not a "diameter" if a longer distance between two wall locations can be found that extends parallel to the short distance. The minimum diameter d is the smallest "diameter" based on this definition. The maximum diameters D of the auxiliary lumens 392 and 394 are generally larger than known pusher catheter lumens in order to provide access for two different elongated devices as explained below.

Notably, while the two oblong auxiliary lumens 392 and 394 are shown as identical in cross-section and having identical elongated devices disposed therein, the cross-sections may differ, depending on the intended use. Generally, for packaging purposes, the maximum diameter D of each of the two oblong auxiliary lumens extends in a generally tangential direction of the pusher catheter, while the minimum diameter d extends in a generally radial direction of the pusher catheter. This optimizes the available cross-sectional space for the guide wire lumen 390 within the pusher catheter 312

In one example, auxiliary lumen 392 may have a dilator 342 disposed therein. Within a dilator 342 there may be a guide wire 346 disposed therein. An access sheath 320 may be coaxially disposed around the dilator 342. The dilator 342, guide wire 346, and access sheath 320 may be used to cannulate a branch vessel (not shown).

Also within the auxiliary lumen 392 may be one or more trigger wires, sheaths, or catheters, subsequently discussed as elongated devices disposed therein. For example, the auxiliary lumen 392 may have space for a sheath 320a and an additional wire 346a disposed therein. In one example the sheath 320a is 6 Fr in diameter and wire 346a is a 0.035" wire. In another example (not shown), instead of sheath 320a, a catheter is disposed in the auxiliary lumen 392. In one example the catheter is 4 Fr in diameter.

In one example auxiliary lumen 394 may have a dilator 334 disposed therein. Within the dilator 334 there may be a guide wire 338 disposed therein. An access sheath 318 may be coaxially disposed around the dilator 334. The dilator 334, guide wire 338, and access sheath 318 may be used to cannulate a branch vessel (not shown).

Also within the auxiliary lumen 394 may be one or more trigger wires, sheaths, or catheters. For example, the auxiliary lumen 394 may have space for a sheath 318a and an additional wire 338a disposed therein. In one example the sheath 318a is 6 Fr in diameter and wire 338a is a 0.035" wire. In another example (not shown), instead of sheath 318a, a catheter is disposed in the auxiliary lumen 394. In one example the catheter is 4 Fr in diameter.

In other words, within auxiliary lumens 392 and 394 there may be both a dilator 342 or 334 and one or more trigger wires, sheaths, or catheters. These components can fit because of the modified tri-lumen pusher catheter's oblong large lumens.

Accordingly, the maximum diameters D of the auxiliary lumens 392 and 394 may, for example, be between approximately 6 mm and 12 mm, selected to be greater than the sum of diameters of the elongated devices disposed therein alongside each other. In order to avoid twisting within the oblong auxiliary catheter, the minimum diameter d is preferably about 4 mm to 6 mm, selected to be greater than the largest single diameter of the elongated devices disposed in the auxiliary lumen, but smaller than the sum of two diameters of the elongated devices disposed therein alongside each other. In this calculation, the diameter of any elongated device extending inside another one of the elongated devices disposed in the auxiliary lumens 392 and 394 has no effect on the selection of the maximum diameter D of the auxiliary lumens, through which it extends, because its lateral movement is delimited by the surrounding elongated device.

For example, the maximum diameter D of auxiliary lumen 392 is determined by the diameters of access sheath 320 and sheath 320a, while the minimum diameter d perpendicular to the maximum diameter D is determined by the diameter of access sheath 320 which is greater than the diameter of sheath 320a. The diameters of guide wires 346 and 346a or of dilator 342, for example, have no influence on the cross-section of the oblong auxiliary lumen 392.

Figure 18:
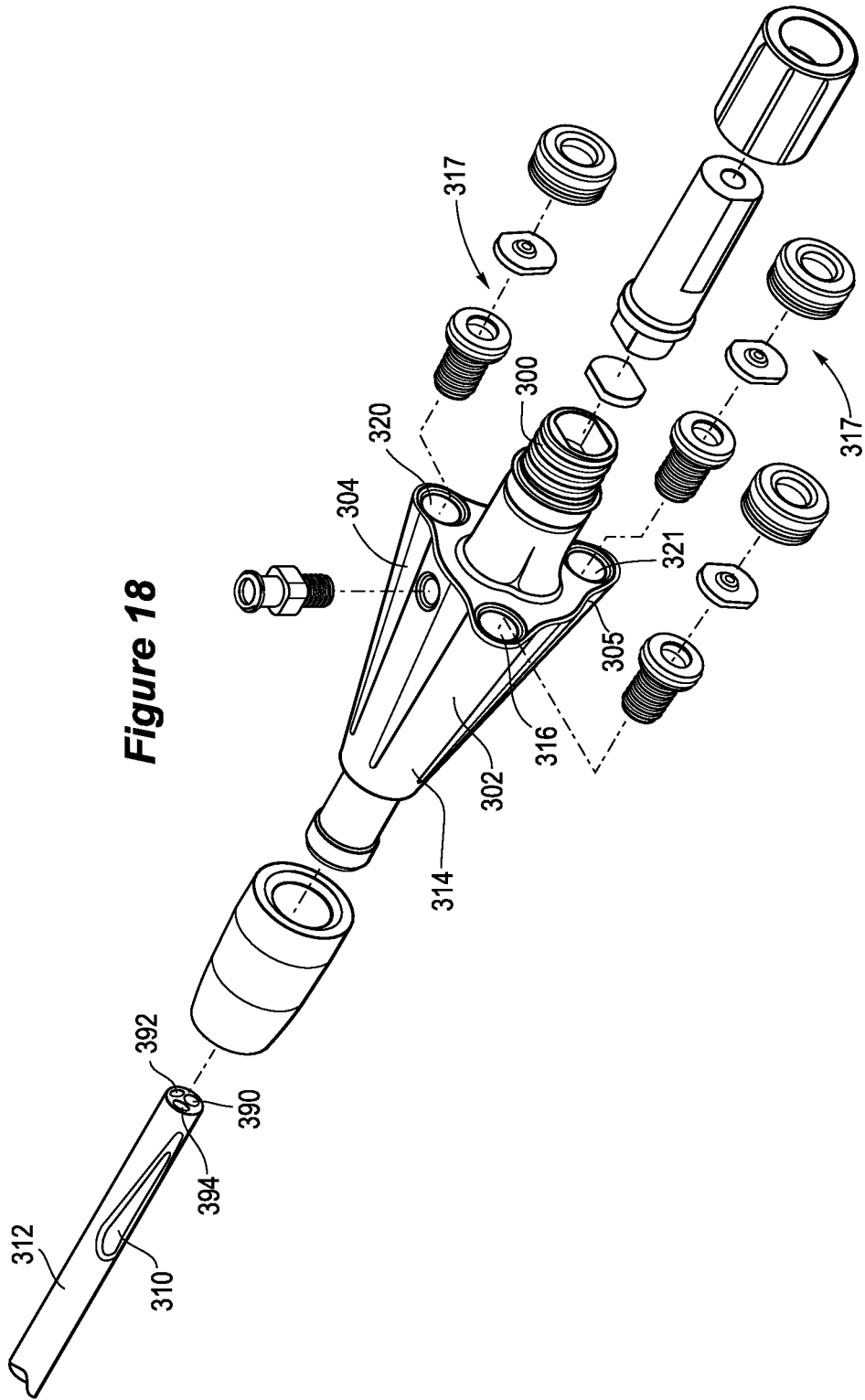
FIG. 18 shows an exploded view of a manifold of an embodiment of the present disclosure.

FIG. 18 shows an exploded view of a manifold 314 of an embodiment of the present disclosure. The manifold 314 has a through bore 300 and angled side ports 302, 304, 305. The pusher catheter 314 has three lumens (as described above in FIG. 17) including the guide wire lumen 390, which is off-set from the center of the pusher catheter to allow for two auxiliary lumens 394 and 392. The pusher catheter 312 may have two or more side apertures 310 (note: only 1 is shown in FIG. 18) which open from the side of the pusher catheter into the respective lumens 390, 392 and 394. These side apertures 310 may be elongate and tapered towards the distal end of the pusher catheter 314. When the pusher catheter 314 is pushed into the through bore 300 of the manifold 314 the side apertures 310 in the pusher catheter align with the respective angled side ports 302, 304, and 305. In one example, angled side port 302 provides an uninterrupted lumen from the access port 316 for the first access sheath 318 into the pusher lumen 394. In second example, angled side port 304 provides an uninterrupted lumen from the access port 320 for a second access sheath 322 into the pusher lumen 392. In a third example, the angled side port 305 provides an uninterrupted lumen from the access port 321 for one or more trigger wires, sheaths, or catheters found in the auxiliary lumens 392 and 394. Each of the access ports 316, 320, and 321 may have a hemostatic seal 317.

Figure 19:
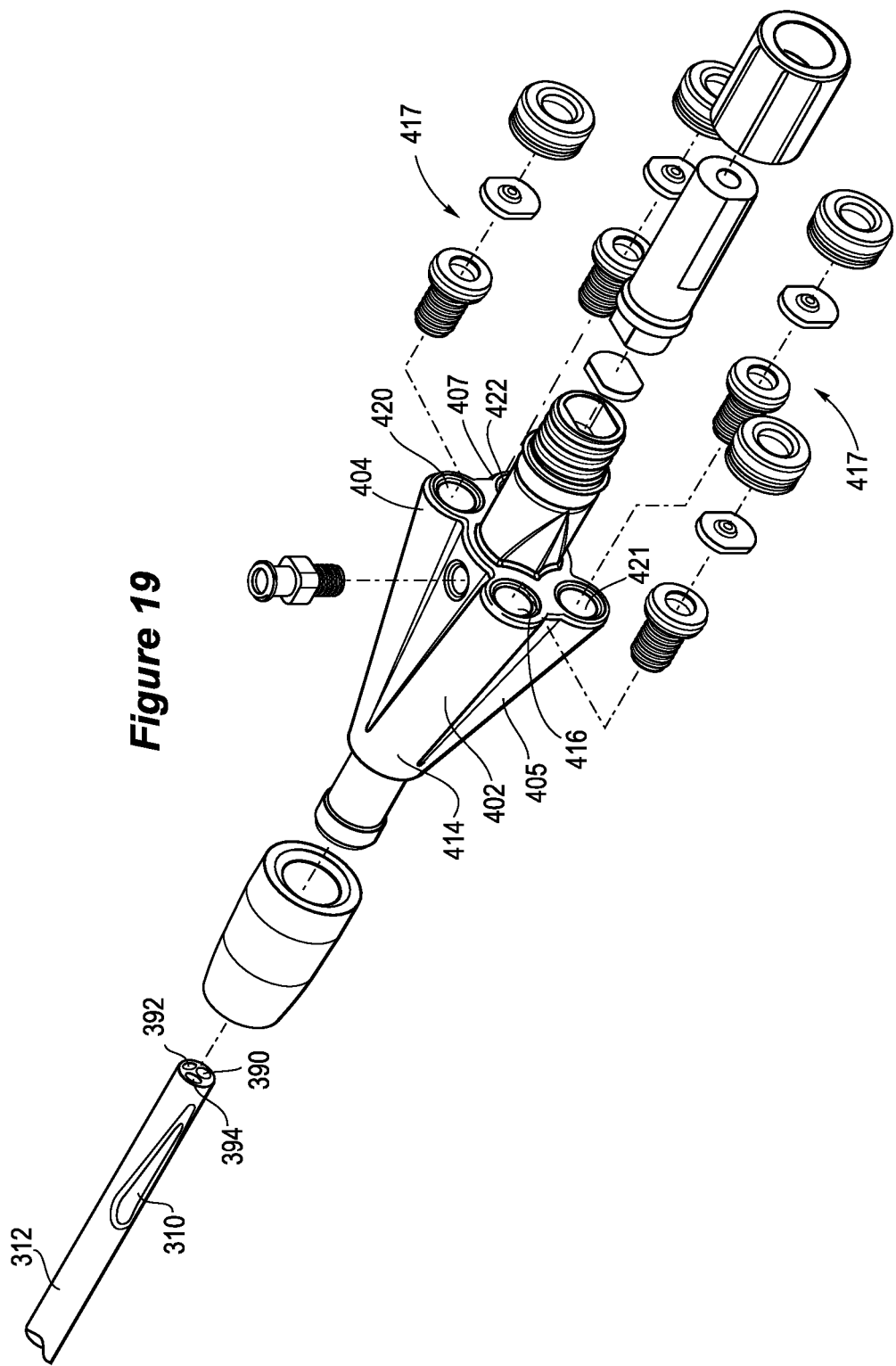
FIG. 19 shows an exploded view of a manifold of an embodiment of the present disclosure.

FIG. 19 shows an exploded view of a manifold of an embodiment of the present disclosure.

The manifold 414 is similar to the manifold 314 shown in FIG. 18, except that it has four angled side ports (instead of three). Manifold 414 has a through bore 400 and four angled side ports 402, 404, 405 and 407. The pusher catheter 312 may have two or more side apertures 310 (note: only 1 is shown in FIG. 19) which open from the side of the pusher catheter into the respective lumens 390, 392 and 394. These side apertures 310 may be elongate and tapered towards the distal end of the pusher catheter 314. When the pusher catheter 314 is pushed into the through bore 400 of the manifold 414 the side apertures 310 in the pusher catheter align with the respective angled side ports 402, 404, 405, and 407. In one example, angled side port 402 provides an uninterrupted lumen from the access port 416 for the first access sheath 318 into the pusher lumen 394. In second example, angled side port 404 provides an uninterrupted lumen from the access port 420 for a second access sheath 322 into the pusher lumen 392. In a third example, the angled side port 405 provides an uninterrupted lumen from the access port 421 for one or more additional trigger wires, sheaths, or catheters found in the auxiliary lumen 392. In a fourth example, the angled side port 407 provides an uninterrupted lumen from the access port 422 for one or more additional trigger wires, sheaths, or catheters found in the auxiliary lumen 394. Each of the access ports 416, 420, 421 and 422 may have a hemostatic seal 417.

The embodiments shown in FIGS. 17-19 and described above may allow preloading of multiple vessels. In one example, it may allow access to four branch vessels and placement of four branch stents in those vessels may occur from an ipsilateral approach. For example, sheaths could be in only two of the branches and stiff wire guides in the remaining vessels as the graft is fully deployed. Alternatively, all of the vessels could be preloaded and some could be chosen to be accessed from an ipsilateral approach and others from a contralateral approach.

It is seen that by this disclosure an arrangement is provided, by which access sheaths may extend through the introduction device and are able to be separately manipulated to enable access to renal or other arteries within the vasculature of a patient.

The invention claimed is:

1. A stent graft delivery device having at least two non-concentric elongate devices preloaded with a stent graft on the delivery device, the stent graft delivery device comprising:
   a guide wire catheter having a guide wire lumen therethrough;
   a handle assembly at a distal end of the guide wire catheter, the handle assembly including a manifold;
   a nose cone dilator at a proximal end of the guide wire catheter;
   a pusher catheter extending from the manifold towards the nose cone dilator, the pusher catheter comprising a longitudinal pusher lumen therethrough and at least two longitudinal auxiliary lumens of an oblong cross-section, the pusher catheter completely enclosing the at least two longitudinal auxiliary lumens and the longitudinal pusher lumen radially, a sheath disposed coaxially over the pusher catheter and the stent graft, the guide wire catheter extending through the pusher lumen and the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;
   the stent graft comprising a stent structure, graft material having a side wall, at least two fenestrations in the side wall of the graft material, a proximal end, a distal end and a lumen therethrough;
   the manifold comprising at least two side ports and a through bore, the at least two side ports extending distally at an angle from the through bore;
   the pusher catheter further comprising at least two apertures near the distal end of the pusher catheter and the at least two apertures opening respectively into an auxiliary lumen of the at least two longitudinal auxiliary lumens, the pusher catheter being in communication with the through bore of the manifold such that the at least two apertures communicate respectively with the at least two side ports;
   wherein at least one of the at least two non-concentric elongate devices is within a respective one of the at least two auxiliary lumens, wherein at least one of the at least two non-concentric elongate devices extends through one of the at least two side ports, into the manifold from external thereof, into the distal end of the stent graft, through the lumen of the stent graft, and out of a respective one of the at least two fenestrations
   wherein the at least two longitudinal auxiliary lumens of an oblong cross-section each have a maximum diameter D extending in a generally tangential direction of the pusher catheter and a minimum diameter d, less than the maximum diameter D, extending in a generally radial direction of the pusher catheter;
   wherein the maximum diameter D is greater than the sum of diameters of the at least two non-concentric elongate devices disposed alongside each other within each of the at least two auxiliary lumens, and, to avoid twisting of the at least two non-concentric elongate devices within each of the at least two auxiliary lumens, the minimum diameter d is greater than the largest single diameter of the at least two non-concentric elongate devices disposed in each of the at least two auxiliary lumens, but smaller than the sum of two diameters of the at least two non-concentric elongate devices.

2. The stent graft delivery device of claim 1, wherein the at least two non-concentric elongate devices comprise an indwelling access sheath and a wire not disposed within the sheath.

3. The stent graft delivery device of claim 2, wherein the indwelling access sheath is at least 6 Fr in diameter.

4. The stent graft delivery device of claim 1, wherein the at least two longitudinal auxiliary lumens is each configured to hold an indwelling access sheath and an additional catheter not disposed within the indwelling access sheath.

5. The stent graft delivery device of claim 4, wherein the additional catheter is at least 4 Fr in diameter.

6. The stent graft delivery device of claim 4, wherein each indwelling access sheath is configured to receive therethrough a further delivery device comprising a side arm stent.

7. The stent graft delivery device of claim 1, wherein each side port has a hemostatic seal assembly and the at least two non-concentric elongate devices extends through the respective hemostatic seal assembly.

8. The stent graft delivery device of claim 1, wherein the stent graft has a scallop in the proximal end of the stent graft.

9. The stent graft delivery device of claim 1, further comprising a distally facing capsule at a distal end of the nose cone dilator, wherein the proximal end of the stent graft is releasably retained within the distally facing capsule.

10. The stent graft delivery device of claim 1, wherein the handle assembly comprises a proximal handle portion and a distal handle portion, the distal handle portion being movable longitudinally with respect to the proximal handle portion, the guide wire catheter extending through each of the distal handle portion and the proximal handle portion, the nose cone dilator and the distal handle portion being movable longitudinally with respect to the proximal handle portion whereby the nose cone dilator can be retracted or advanced independently of the manifold and pusher catheter.

11. The stent graft delivery device of claim 1, wherein the maximum diameter D of each of the at least two longitudinal auxiliary lumens extends in a direction enclosing a greater angle with a radial direction of the pusher catheter than the minimum diameter d.

12. The stent graft delivery device of claim 11, wherein the maximum diameter D is greater than the minimum diameter d by a factor in a range of 1.4 through 2.

13. The stent graft delivery device of claim 1, wherein the maximum diameter D is from about 6 mm to about 12 mm and the minimum diameter d is from about 4 mm to about 6 mm.

14. The stent graft delivery device of claim 1, wherein the manifold comprises at least 3 side ports, two of which being jointly in communication with a common one of the at least two auxiliary lumens.

15. The stent graft delivery device of claim 1, wherein the manifold comprises at least four side ports, two of which being jointly in communication with a common one of the at least two auxiliary lumens.

16. The stent graft delivery device of claim 1, further comprising a catheter and a wire within each of the at least two auxiliary lumens.

17. The stent graft delivery device of claim 1, wherein each of the at least two auxiliary lumens has a first end angled toward each other and a second end angled away from each other.

18. A method of placing a stent graft in a body vessel at a treatment site, comprising:
   introducing a proximal end of a stent graft delivery device into a body vessel and advancing the stent graft delivery device to the treatment site, the stent graft delivery device comprising:
      a guide wire catheter having a guide wire lumen therethrough;
      a handle assembly at a distal end of the guide wire catheter, the handle assembly including a manifold;
      a nose cone dilator at a proximal end of the guide wire catheter, the nose cone dilator comprising a distally facing capsule on the distal end of the nose cone dilator;
      a pusher catheter extending from the manifold towards the nose cone dilator, the pusher catheter comprising a longitudinal pusher lumen therethrough and at least two auxiliary lumens having an oblong cross-section, the pusher catheter completely enclosing the at least two auxiliary lumens and the longitudinal pusher lumen radially;
      a sheath disposed coaxially over the pusher catheter and the stent graft,
      the guide wire catheter extending through the longitudinal pusher lumen, the guide wire catheter able to move longitudinally and rotationally with respect to the pusher catheter, the pusher catheter comprising a proximal end spaced distally from the nose cone dilator and thereby defining between the proximal end of the pusher catheter and the nose cone dilator a stent graft retention region;
      the stent graft comprising a stent structure, graft material having a side wall, at least two fenestrations in the side wall of the graft material, a proximal end a distal end and a lumen therethrough;
      the manifold comprising at least two side ports and a through bore, the at least two side ports extending distally at an angle from the through bore,
      the pusher catheter further comprising at least two apertures near the distal end of the pusher catheter and the at least two apertures opening respectively into the at least two auxiliary lumens, the pusher catheter being in communication with the through bore of the manifold such that the at least two apertures communicate respectively with the at least two side ports;
      at least two non-concentric elongate devices each disposed within a respective auxiliary lumen of the at least two auxiliary lumens, wherein one of the at least two non-concentric elongate devices extends through one of the at least two side ports, into the manifold from external thereof, into the distal end of the stent graft, through the lumen of the stent graft, and out one of the at least two fenestrations;
      wherein the at least two longitudinal auxiliary lumens of an oblong cross-section each have a maximum diameter D extending in a generally tangential direction of the pusher catheter and a minimum diameter d, less than the maximum diameter D, extending in a generally radial direction of the pusher catheter;
      wherein the maximum diameter D is greater than the sum of diameters of the at least two non-concentric elongate devices disposed alongside each other within each of the at least two auxiliary lumens, and, to avoid twisting of the at least two non-concentric elongate devices within each of the at least two auxiliary lumens, the minimum diameter d is greater than the largest single diameter of the at least two non-concentric elongate devices disposed in each of the at least two auxiliary lumens, but smaller than the sum of two diameters of the at least two non-concentric elongate devices;
   partially withdrawing the sheath from the stent graft;
   advancing a guide wire through each of the at least two non-concentric elongate devices, out of the at least two fenestrations and into a respective target branch vessel branching from the body vessel;
   advancing at least one of the two non-concentric elongate devices to the target branch vessel;
   releasing the proximal end of the stent graft;
   advancing a side arm stent through at least one of the two non-concentric elongate devices and at least partially out of one of the at least two fenestrations and into the respective target branch vessel, the side arm stent having a proximal end and a distal end;
   expanding the side arm stent within the target vessel with a balloon;
   flaring the proximal end of the side arm stent within the lumen of the stent graft.

19. The method of claim 18, further comprising a catheter within each of the at least two auxiliary lumens.

20. The method of claim 18, further comprising advancing a second guide wire through at least one of the at least two auxiliary lumens.

21. The method of claim 18, wherein the stent graft comprises four fenestrations.

* * * * *